United States Patent [19]

Goldman et al.

[11] 4,154,947

[45] May 15, 1979

[54] HETEROCYCLIC SUBSTITUTED BENZYLIDENEAMINOGUANIDINES

[75] Inventors: Leon Goldman, Nanuet; Joseph W. Marsico, Jr., Pearl River, both of N.Y.

[73] Assignee: American Cyanamid Company, Stamford, Conn.

[21] Appl. No.: 886,211

[22] Filed: Mar. 13, 1978

[51] Int. Cl.² ............... C07D 213/73; C07D 231/06; C07D 327/04; C07D 333/10
[52] U.S. Cl. .................................. 542/417; 260/566 B
[58] Field of Search ..................... 542/417; 260/564 F, 260/566 B

[56] References Cited

U.S. PATENT DOCUMENTS

| 3,516,995 | 6/1970 | Houlihan et al. | 542/417 |
| 3,816,531 | 6/1974 | Bruce et al. | 260/564 F |
| 3,959,476 | 5/1976 | Eriksson et al. | 542/417 X |

FOREIGN PATENT DOCUMENTS 1036987 7/1966 United Kingdom ................ 260/564 F

OTHER PUBLICATIONS

Mull et al., "Guanidines with Antihypertensive Activity", in Chem. Abs. CA. 55:16418(b), 1961.

*Primary Examiner*—Allen B. Curtis
*Attorney, Agent, or Firm*—Edward A. Conroy, Jr.

[57] ABSTRACT

This disclosure describes novel substituted benzylideneaminoguanidines useful as anti-hypertensive agents and as diuretics.

6 Claims, No Drawings

HETEROCYCLIC SUBSTITUTED BENZYLIDENEAMINOGUANIDINES

BRIEF SUMMARY OF THE INVENTION

This invention relates to new organic compounds and, more particularly, is concerned with novel substituted benzylideneaminoguanidines which may be represented by the following structural formula:

wherein $R_1$ is 2,6-dimethylphenyl or 2,6-dichlorophenyl and $R_2$ is 2-pyridyl, 3-pyridyl, 4-pyridyl, 2-furyl, 2-thienyl, 4-methyl-2-thiazolyl or 2-pyrazinyl. The invention also includes novel compositions of matter containing the above-defined compounds useful as hypotensive agents and/or as diuretics and the method of meliorating hypertension and/or enhancing the excretion of sodium ions in mammals therewith.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, N,N-dimethylformamide, acetone, chloroform, ethyl acetate, and the like. They are appreciably soluble in non-polar organic solvents such as toluene, carbon tetrachloride, and the like but are relatively insoluble in water. The organic bases of this invention form non-toxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

The novel compounds of the present invention may exist in other tautomeric forms as follows:

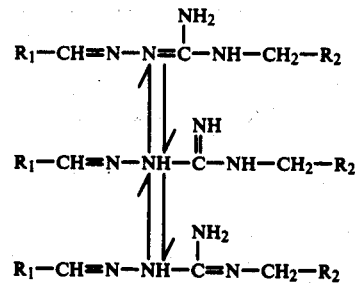

For purposes of this invention, all such tautomeric forms are equivalent.

The novel compounds of the present invention are physiologically active and therefore useful in the pharmaceutical field. In particular, the compounds of this invention are useful because they possess not only long lasting hypotensive activity but also diuretic and natriuretic properties. They differ from most of the known effective diuretic agents, however, in that the compounds of this invention greatly enhance the excretion of sodium ions with only a slight increase in excretion of potassium ions. The potassium loss, which is caused by known diuretics, often results in a severe muscular weakness. Since the compounds of this invention are essentially free of this potassium depletion effect, they have this decided advantage as diuretics. As diuretic agents, they can be used for the treatment of edema, hypertension and other diseases known to be responsive to this therapy.

The novel compounds of the present invention were shown to possess oral activity in vivo as hypotensive agents and as diuretics (producing significant water diuresis and Na+ loss but with sparing of K+) as determined in the following procedure. One to three adult spontaneously hypertensive rats are dosed by gavage with a test compound at a dose of 100 mg./kg. of body weight at zero hour. The 0–5 hour urine is collected and Na+, K+ and Cl− concentrations analyzed. A second identical dose of test compound is given without NaCl loading at 24 hours. The mean arterial blood pressure is measured directly by femoral artery puncture at 28 hours. The results with representative compounds of the present invention are given in Table I below wherein the reduction in mean arterial blood pressure is represented as:

4+ = 100–110 mm.
3+ = 111–120 mm.
2+ = 121–130 mm.
1+ = 131–135 mm.

as contrasted to a control value 165 mm. The sodium, potassium, and chloride levels are given in terms of milliequivalents (meq.) per 5 hours with a normal sodium control being 0.60 milliequivalents per 5 hours.

TABLE I

| Compound | Reduction in mean arterial blood pressure | Diuretic Results Urine Volume ml./5 Hr. | Total Meq./5 Hours | | |
|---|---|---|---|---|---|
| | | | Na+ | K+ | Cl− |
| 1-(2,6-Dichlorobenzylideneamino)-3-(2-pyridylmethyl)guanidine | 3+ | 21.0 | 1.86 | 0.50 | 2.08 |
| 1-(2,6-Dichlorobenzylideneamino)-3-(3-pyridylmethyl)guanidine | 4+ | 19.5 | 1.58 | 0.47 | 1.94 |
| 1-(2,6-Dichlorobenzylideneamino)-3-(3-pyridylmethyl)guanidine dihydrochloride | 2+ | 21.5 | 2.12 | 0.44 | 2.24 |
| 1-(2,6-Dichlorobenzylideneamino)-3-(4-pyridylmethyl)guanidine | 3+ | 28.0 | 2.42 | 0.58 | 2.58 |

TABLE I-continued

| Compound | Reduction in mean arterial blood pressure | Diuretic Results Urine Volume ml./5 Hr. | Total Meq./5 Hours Na+ | K+ | Cl− |
|---|---|---|---|---|---|
| 1-(2,6-Dichlorobenzylideneamino)-3-furfurylguanidine | 4+ | 11.8 | 0.96 | 0.46 | 1.17 |
| 1-(2,6-Dichlorobenzylideneamino)-3-(2-thenyl)guanidine | 4+ | 13.5 | 1.28 | 0.58 | 1.49 |
| 1-(2,6-Dichlorobenzylideneamino)-3-furfurylguanidine hydriodide | 2+ | 9.5 | 0.75 | 0.40 | 0.98 |
| 1-(2,6-Dichlorobenzylideneamino)-3-[(4-methyl-2-thiazolyl)methyl]guanidine | 1+ | 17.2 | 1.12 | 0.45 | 1.29 |
| 1-(2,6-Dichlorobenzylideneamino)-3-(2-pyrazinylmethyl)guanidine | 2+ | 22.2 | 1.97 | 0.36 | 2.23 |
| 1-(2,6-Dimethylbenzylideneamino)-3-(2-pyridylmethyl)guanidine hydriodide | 1+ | 9.0 | 0.77 | 0.71 | 0.98 |
| 1-(2,6-Dimethylbenzylideneamino)-3-(4-pyridylmethyl)guanidine hydriodide | 4+ | 15.3 | 1.29 | 0.72 | 1.53 |

The novel compounds of the present invention have thus been shown to be valuable hypotensive and diuretic agents of low toxicity when administered orally. The amount of a single dose or of a daily dose to be given will vary but should be such as to give a proportionate dosage of from about 5 mg. to about 100 mg. per day for a subject of about 70 kg. body weight. The dosage regimen may be adjusted to provide the optimum therapeutic response; for example, doses of 1.0–25 mg. may be administered on a 4 times a day regimen or the dose may be proportionately increased as indicated by the exigencies of the therapeutic situation.

The novel compounds of the present invention may be administered as active components of compositions for administration in unit dosage form as tablets, pills, capsules, powders, granules, oral solutions or suspensions and the like. For preparing solid compositions such as tablets, the principal active ingredient is mixed with conventional tableting ingredients such as corn starch, lactose, sucrose, sorbitol, talc, stearic acid, magnesium stearate, dicalcium phosphate, gums, and functionally similar materials as pharmaceutical diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelop over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

The liquid forms in which the novel compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use, as disclosed in detail in this specification, these being features of the present invention. Examples of suitable oral unit dosage forms in accord with this invention are tablets, capsules, pills, powders, granules, wafers, teaspoonfuls, dropperfuls, ampules, vials, segregated multiples of any of the foregoing and other forms as herein described.

The novel compounds of the present invention may be readily prepared in accordance with the following reaction scheme:

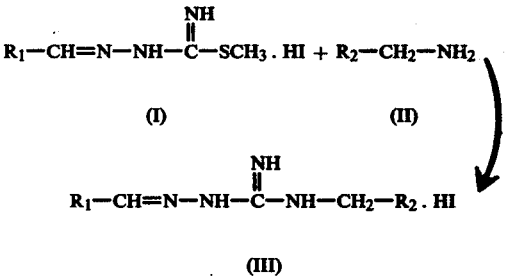

$$R_1-CH=N-NH-\overset{NH}{\underset{\|}{C}}-SCH_3 \cdot HI + R_2-CH_2-NH_2$$

(I)  (II)

$$R_1-CH=N-NH-\overset{NH}{\underset{\|}{C}}-NH-CH_2-R_2 \cdot HI$$

(III)

wherein $R_1$ and $R_2$ are as herein above defined. In accordance with this reaction scheme, an appropriate methyl 3-(2,6-disubstituted-benzylidene)thiocarbazimidate hydroiodide (I) is treated with a primary amine (II) in ethanol as solvent at the reflux temperature for 4–24 hours to provide the compounds of the present invention (III) which are recovered and purified by conventional means. An alternate procedure is set forth in the following reaction scheme:

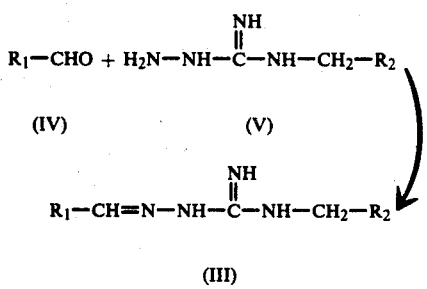

wherein $R_1$ and $R_2$ are as herein above defined. In accordance with this reaction scheme an appropriate 2,6-disubstituted-benzaldehyde (IV) is condensed with a 1-amino-3-substituted-guanidine (V) in glacial acetic acid as solvent at steam bath temperature (90°–100° C.) for a few hours or more to provide the compounds of the present invention (III) which again are recovered and purified by conventional methods.

The invention will be described in greater detail in conjunction with the following specific examples.

EXAMPLE 1

Preparation of 1-(2,6-Dichlorobenzylideneamino)-3-(2-pyridylmethyl)guanidine

A solution of 5.85 g. of methyl 3-(2,6-dichlorobenzylidene)thiocarbazimidate hydriodide (U.S. Pat. No. 3,657,337) and 3.24 g. of 2-(aminomethyl)pyridine in 25 ml. of absolute ethanol is heated under reflux for 20 hours and diluted while hot with 75 ml. of water, causing the separation of an oil. On standing, the oil crystallizes and filtration gives 5.00 g. of pale yellow crystals, m.p. 125°–140° C. Recrystallization from aqueous ethanol gives the desired compound as pale yellow crystals, m.p. 159.5°–161° C.

EXAMPLE 2

Preparation of 1-(2,6-Dichlorobenzylideneamino)-3-(3-pyridylmethyl)guanidine

A mixture of 5.85 g. of methyl 3-(2,6-dichlorobenzylidene)thiocarbazimidate hydriodide, 3.24 g. of 3-(aminomethyl)pyridine and 25 ml. of absolute ethanol is heated under reflux for 24 hours and diluted while hot with 75 ml. of water. After cooling, an oil separates and crystallizes. The mixture is chilled overnight and the crystals are separated and recrystallized from 100 ml. of 50% aqueous ethanol to give the desired product as pale yellow crystals, m.p. 148°–151° C.

EXAMPLE 3

Preparation of 1-(2,6-Dichlorobenzylideneamino)-3-(3-pyridylmethyl)guanidine dihydrochloride A solution of 5.85 g. of methyl 3-(2,6-dichlorobenzylidene)thiocarbazimidate hydriodide and 1.62 g. of 3-(aminomethyl)pyridine in 25 ml. of absolute ethanol is heated under reflux for 47 hours. To the resulting solution is added 3.00 ml. of 5N sodium hydroxide and evaporation under reduced pressure gives a light brown crystalline residue. The residue is dissolved in 100 ml. of dichloromethane:methanol (95:5) and chromatographed on a column (2.8 × 35 cm.) of silica gel; 200 ml. cuts are taken. Evaporation under reduced pressure of combined cuts 2–4 gives 4.70 g. of crude product as a light tan foam. The foam is dissolved in 25 ml. of absolute ethanol and 7.5 ml. of 5.25N methanolic hydrogen chloride is added. The resulting solution is evaporated under reduced pressure and the residual gum is crystallized from absolute ethanol-acetone. After chilling, filtration gives 3.83 g. of light tan crystals. Recrystallization from 1:1 methanol:acetonitrile gives the desired product as colorless crystals, m.p. 235°–239° C. (dec.).

EXAMPLE 4

Preparation of 1-(2,6-Dichlorobenzylideneamino)-3-(4-pyridylmethyl)guanidine

A solution of 5.85 g. of methyl 3-(2,6-dichlorobenzylidene)thiocarbazimidate hydriodide and 3.24 g. of 4-(aminomethyl)pyridine in 25 ml. of absolute ethanol is heated under reflux for 24 hours and then diluted with 75 ml. of water, causing the separation of an oil. On standing, the oil crystallizes. Filtration and recrystallization from aqueous ethanol gives the desired product as colorless crystals, m.p. 159°–161° C.

EXAMPLE 5

Preparation of 1-Amino-3-furfurylguanidine hydriodide

A solution of 23.3 g. of methyl thiocarbazimidate hydriodide and 9.71 g. of furfurylamine in 60 ml. of water is heated at 100° C. for 0.5 hours and then evaporated under reduced pressure to give a reddish-orange oil. The oil is crystallized from an absolute ethanol-ether mixture and, after chilling, filtration gives 16.3 g. of pink colored crystals. A suspension of the crystals in 50 ml. of absolute ethanol is warmed slightly to dissolve all but insoluble red crystals which are filtered off. The mother liquor is diluted with ether to crystallization and, after chilling, filtration gives 11.2 g. of light pink crystals. Recrystallization of a 4.00 g. sample from absolute ethanol-ether gives 3.27 g. of 1-amino-3-furfurylguanidine hydriodide as nearly colorless crystals, m.p. 98°–99.5° C.

EXAMPLE 6

Preparation of 1-(2,6-Dichlorobenzylideneamino)-3-furfurylguanidine

A solution of 1.75 g. of 2,6-dichlorobenzaldehyde and 2.82 g. of 1-amino-3-furfurylguanidine hydriodide in 15 ml. of glacial acetic acid is heated at 100° C. for one hour, cooled, and diluted with absolute ether until crystallization occurs. Filtration gives 3.51 g. of gray-colored crystals. The crystals are dissolved by warming in absolute ethanol and the solution is treated with excess 10N sodium hydroxide and diluted with water to turbidity. Chilling and filtration give 2.00 g. of nearly colorless crystals. Two recrystallizations from aqueous ethanol, using activated charcoal, give the desired product as colorless crystals, m.p. 134°–135.5° C.

EXAMPLE 7

Preparation of 1-(2,6-Dichlorobenzylideneamino)-3-fufurylguanidine hydriodide

A solution of 1.31 g. of 2,6-dichlorobenzaldehyde, 2.12 g. of 1-amino-3-furfurylguanidine hydriodide and 0.5 ml. of glacial acetic acid in 12.0 ml. of 66% aqueous ethanol is heated under reflux for 24 hours and then evaporated under reduced pressure to a reddish-brown gum. The gum is crystallized from a mixture of ethyl acetate-ethanol to give 2.32 g. of tan crystals. Recrystallization from ethyl acetate-ethanol gives the desired product as colorless crystals, m.p. 138°–139° C.

EXAMPLE 8

Preparation of 1-(2,6-Dichlorobenzylideneamino)-3-(2-thenyl)guanidine

A solution of 5.85 g. of methyl 3-(2,6-dichlorobenzylidene)thiocarbazimidate hydriodide and 3.39 g. of 2-(aminomethyl)thiophene in 25 ml. of absolute ethanol is heated under reflux for 16 hours, diluted with water and excess 10N sodium hydroxide is added. After standing, crystallization occurs, and filtration gives 3.50 g. of nearly colorless crystals. Recrystallization from aqueous ethanol gives the desired product as colorless crystals, m.p. 135°–137° C.

EXAMPLE 9

Preparation of 1-(2,6-Dichlorobenzylideneamino)-3-[(4-methyl-2-thizaolyl)methyl]guanidine A solution of 9.75 g. of methyl 3-(2,6-dichlorobenzylidene)thiocarbazimidate hydriodide and 4.12 g. of 2-(aminomethyl)-4-methylthiazole dihydrochloride [A. A. Goldman and W. Kelly, J. Chem. Soc., 1372 (1947)] in 100 ml. of absolute ethanol containing 2.00 g. of sodium hydroxide is heated at reflux for 18 hours and then filtered while hot. The filtrate is diluted with water to a volume of 400 ml. to give a gummy precipitate which is crystallized from a mixture of methanol and ethyl ether to give 1.80 g. of crystals. The crystals are extracted into chloroform from aqueous alkali and then chromatographed on 130 g. of dry column grade alumina with ethyl acetate to give 0.280 g. of the desired product as colorless crystals, m.p. 147°–149° C.

EXAMPLE 10

Preparation of 1-Amino-3-(pyrazinylmethyl)guanidine hydriodide

A solution of 3.66 g. of methyl thiocarbazimidate hydriodide and 3.42 g. of (aminomethyl)pyrazine [A. Hirschberg and P. Mattner, J. Med. Chem., 11, 911 (1961)] in 50 ml. of absolute ethanol is heated at reflux for 20 hours and then concentrated to dryness under reduced pressure to give the desired product as an orange solid.

EXAMPLE 11

Preparation of 1-(2,6-Dichlorobenzylideneamino)-3-(pyrazinylmethyl)guanidine

A solution of 2.83 g. of 2,6-dichlorobenzaldehyde and 1-amino-3-(pyrazinylmethyl)guanidine hydriodide from Example 10 in 50 ml. of absolute ethanol and 5.0 ml. of glacial acetic acid is heated at reflux for 4 hours. The cooled solution is made basic by addition of 10N sodium hydroxide and extracted with ether. The ether extract is evaporated to give a residual orange gum which is crystallized from absolute ethanol to give the desired product as colorless crystals, m.p. 168°–169° C.

EXAMPLE 12

Preparation of 1-(2,6-Dimethylbenzylideneamino)-3-(2-pyridylmethyl)guanidine hydriodide A mixture of 2.93 g. of 1-amino-3-(2-pyridylmethyl)guanidine hydriodide and 1.34 g. of 2,6-dimethylbenzaldehyde [G. Lock and K. Schmidt, J. Prakt. Chem., 140, 229 (1934)] is dissolved in 5 ml. of glacial acetic acid at 100° C. After 2 hours the solidified reaction is triturated with water and filtered. Crystallization from absolute ethanol gives the desired product as colorless needles, m.p. 184°–186° C.

EXAMPLE 13

Preparation of 1-(2,6-Dimethylbenzylideneamino)-3-(4-pyridylmethyl)guanidine hydriodide A mixture of 2.93 g. of 1-amino-3-(4-pyridylmethyl)guanidine hydriodide and 1.34 g. of 2,6-dimethylbenzaldehyde in 5 ml. of glacial acetic acid is heated at 100° C. After 2 hours the solidified reaction mixture is triturated with water and filtered. Crystallization from absolute ethanol gives the desired product as colorless granular crystals, m.p. 197°–200° C.

EXAMPLE 14

| Preparation of 50 mg. Tablets | | |
|---|---|---|
| Per Tablet | | Per 10,000 Tablets |
| 0.50 g. | 1-(2,6-Dichlorobenzylidene-amino)-3-(3-pyridylmethyl)-guanidine dihydrochloride | 500 g. |
| 0.80 g. | Lactose | 800 g. |
| 0.10 g. | Corn starch (for mix) | 100 g. |
| 0.008 g. | Corn starch (for paste) | 75 g. |
| 0.002 g. | Magnesium stearate (1%) | 15 g. |
| 0.150 g. | | 1490 g. |

The 1-(2,6-dichlorobenzylideneamino)-3-(3-pyridylmethyl)guanidine dihydrochloride, lactose and corn starch (for mix) are blended together. The corn starch (for paste) is suspended in 600 ml. of water and heated with stirring to form a paste. This paste is then used to granulate the mixed powders. Additional water may be used. The wet granules are passed through a No. 8 hand screen, dried at 120° F., passed through a No. 16 screen, lubricated with 1% magnesium stearate and compressed into tablets.

EXAMPLE 15

| Preparation of Oral Suspension | |
|---|---|
| Ingredient | Amount |
| 1-(2,6-Dichlorobenzylideneamino)-3-(2-pyridylmethyl)guanidine | 500 mg. |
| Sorbitol solution (70% NF) | 40 ml. |
| Sodium benzoate | 150 mg. |
| Saccharin | 10 mg. |
| Red dye | 10 mg. |
| Cherry flavor | 50 mg. |
| Distilled water    qs to | 100 ml. |

The sorbitol solution is added to 40 ml. of distilled water and the 1-(2,6-dichlorobenzylideneamino)-3-(2-pyridylmethyl)guanidine is suspended therein. The saccharin, sodium benzoate, flavor and dye are added and dissolved. The volume is adjusted to 100 ml. Each ml. of syrup contains 5 mg. of active ingredient.

We claim:

1. A compound selected from the group consisting of those of the formula:

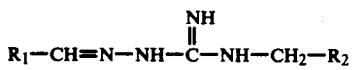

wherein $R_1$ is 2,6-dimethylphenyl or 2,6-dichlorophenyl and $R_2$ is 2-pyridyl, 3-pyridyl, 4-pyridyl, 2-furyl, 2thienyl, 4-methyl-2-thiazolyl or 2-pyrazinyl; the tautomers thereof and the pharmacologically acceptable acid-addition salts thereof.

2. The compound according to claim 1 wherein $R_1$ is 2,6-dimethylphenyl and $R_2$ is 3-pyridyl; 1-(2,6-dimethylbenzylideneamino)-3-(3-pyridylmethyl)guanidine.

3. The compound according to claim 1 wherein $R_1$ is 2,6-dimethylphenyl and $R_2$ is 2-furyl; 1-(2,6-dimethylbenzylideneamino)-3-furfurylguanidine.

4. The compound according to claim 1 wherein $R_1$ is 2,6-dimethylphenyl and $R_2$ is 2-thienyl; 1-(2,6-dimethylbenzylideneamino)-3-(2-thenyl)guanidine.

5. The compound according to claim 1 wherein $R_1$ is 2,6-dimethylphenyl and $R_2$ is 4-methyl-2-thiazolyl; 1-(2,6-dimethylbenzylideneamino)-3-[(4-methyl-2-thiazolyl)methyl]guanidine.

6. The compound according to claim 1 wherein $R_1$ is 2,6-dimethylphenyl and $R_2$ is 2-pyrazinyl; 1-(2,6-dimethylbenzylideneamino)-3-(2-pyrazinylmethyl)guanidine.